United States Patent [19]

Flora et al.

[11] Patent Number: 4,640,132

[45] Date of Patent: Feb. 3, 1987

[54] ENHANCEMENT OF LINEAR SCAN ULTRASONICS

[75] Inventors: John H. Flora; Thomas Powers, Jr., both of Lynchburg, Va.

[73] Assignee: The Babcock & Wilcox Company, New Orleans, La.

[21] Appl. No.: 691,599

[22] Filed: Jan. 15, 1985

[51] Int. Cl.$^4$ ............................................. G01N 29/04
[52] U.S. Cl. ......................................... 73/602; 73/620; 73/628
[58] Field of Search ................. 73/602, 620, 627, 628; 367/52

[56]  References Cited

U.S. PATENT DOCUMENTS 3,651,451  3/1972  Ruehle ................................... 367/52
3,794,827  2/1974  Widess ................................... 367/52

OTHER PUBLICATIONS

*Reflection Seismology*, Waters, 1981, John Wiley & Sons, pp. 285, 193, 194–196.

Primary Examiner—Howard A. Birmiel
Attorney, Agent, or Firm—Vytas R. Matas; Robert J. Edwards

[57] ABSTRACT

An ultrasonic testing method and apparatus stores the reflected ultrasonic signals from each of a plurality of locations along a scan path over a piece of material to be tested. For each individual location, the reflected signal at that location is added to contributing signals from each other location to produce a composite signal which has a good signal-to-noise ratio. The contributing signals from each other location is formed by multiplying the signal of those other locations by a corrective phase shift factor which is a characteristic of a time delay for a reflected signal from the other locations to the individual location of interest. The contributing signal from each other location thus represents a rotated reflected signal from the other locations.

2 Claims, 3 Drawing Figures

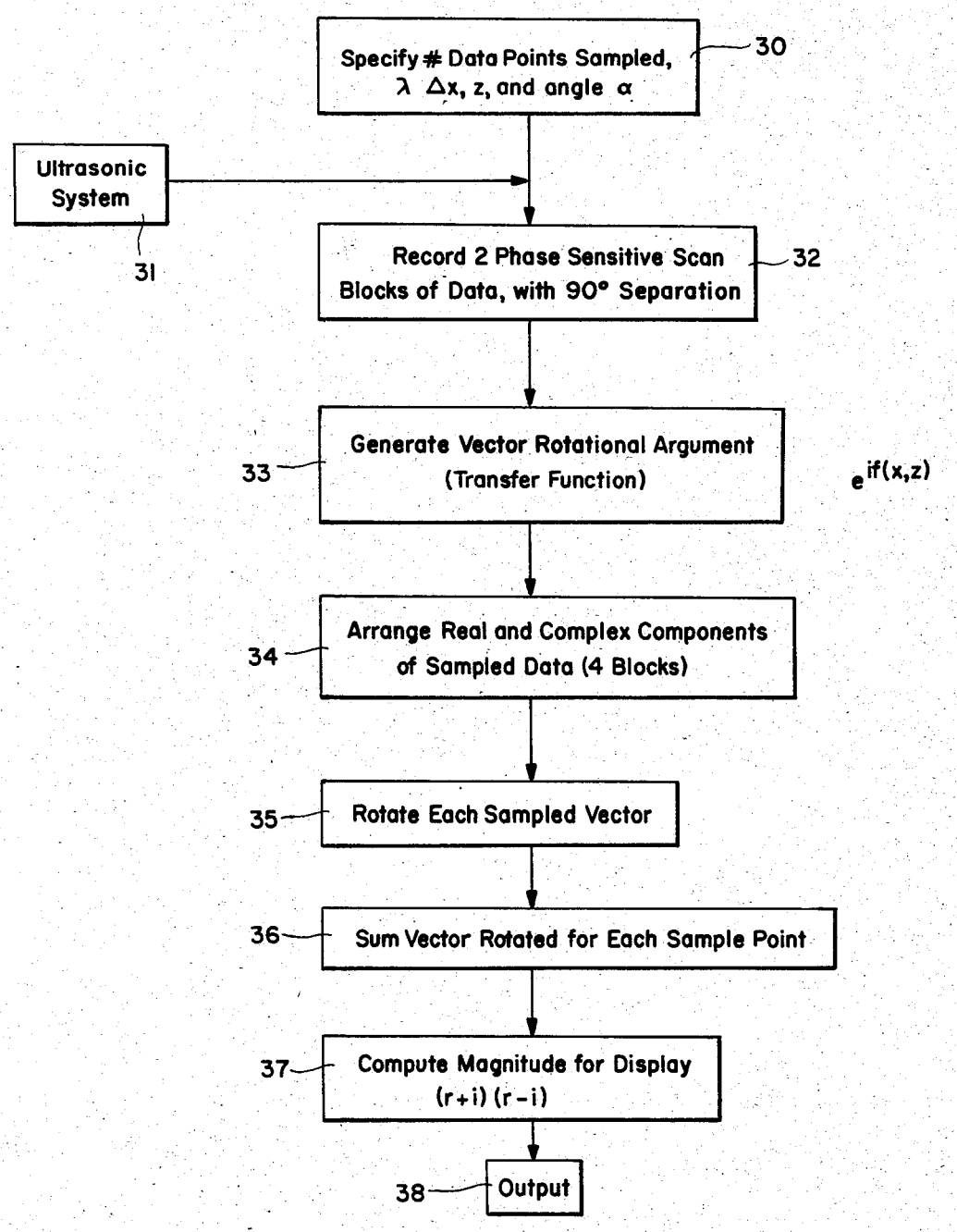

ENHANCEMENT OF LINEAR SCAN ULTRASONICS

FIELD AND BACKGROUND OF THE INVENTION

The present invention relates in general to the field of ultrasonic testing, and in particular to a new and useful apparatus and method for detecting flaws in coarse grained materials in which ultrasonic pulses are detected and stored in a digital memory and a computer or microprocessor is used to multiply the received pulses by a corrective phase shift factor to compensate for a time delay of the ultrasonic pulses from various angles of scan.

In the field of ultrasonic testing, it is known to scan a material to be tested either by using a plurality of transducers spaced around the material or by the use of a single transducer that is physically moved to various positions around the material to be examined. See for example U.S. Pat. No. 3,543,229 to Baum and U.S. Pat. No. 3,990,300 to Kossoff.

It is also known to convert the received ultrasonic signals from ultrasonic test equipment into digital form and to store them in a memory. See for example U.S. Pat. No. 4,163,393 to Gutierrez et al and U.S. Pat. No. 3,857,052 to Beller. The Gutierrez et al reference also teaches that comparisons between signals received from different locations of the transducer may be utilized to test for flaws. Gutierrez however cancels similar signals from the transducers. Beller on the other hand compares signals obtained at different time increments to detect a variation over time at the same point of the material to be tested. Neither reference teaches the multiplication of stored signals by a corrective phase shift factor to compensate for the time delay between the signals and to use the signals in an additive and averaging manner to provide reinforcement of the measured signals which increases a signal to noise ratio as in the present invention. These aspects of the invention will be set forth in greater detail later.

Conventional ultrasonic testing provides time, amplitude and spatial information that is combined through mechanical and electronic apparatus to form so called A, B, and C scans for flaw detection and sizing. The most commonly used technique is time-amplitude, A scan ultrasonic testing. All of these techniques make use of either a continuous wave or pulse excitation and time reference signal. The primary limitations with these techniques are that they only allow discrimination via signal amplitudes, time separation, or spatial separation which are variables extremely sensitive to the flaw orientation, test material properties, and test article geometry.

Typical ultrasonic testing makes use of a relatively narrow beam radiation pattern that is highly directional in material interrogation. When coarse grained materials (i.e., stainless steels, etc.) are encountered, the highly directional radiation patterns of the internal grain structures interact with the transducer pattern to provide high amplitude background signals. These signals are inseparable from those flaws yielding comparable amplitude levels when the conventional techniques are used. Under these conditions the probability of missing flaws and rejecting material due to "false flaws" is very high.

Previous inspection techniques used ultrasonic transducers that made a position-to-position interrogation of these materials where each position was an independent assessment of the material in the path of the beam. This technique has been accepted as adequate for fine grained material inspection but is less than desirable for coarse grained material. In these materials, absorption and scattering of the ultrasonic beam limits flaw detection capabilities to a greater extent than with other materials.

SUMMARY OF THE INVENTION

The present invention is drawn to an ultrasonic scanning system for coarse grained materials which provides increased signal noise ratios. To accomplish this, either a single transducer is scanned over the material to be tested or a transducer array is utilized to transmit and receive ultrasonic signals to and from the test material. The ultrasonic equipment receives the pulses and stores them in digital memory. Means are provided such as a computer or microprocessor for multiplying the received pulses by a corrective phase shift factor to compensate for the time delay of the ultrasonic pulses from the various scan angles. A signal average for each location along the scan is computed which comprises a reinforced signal which provides an increased signal to noise ratio.

According to the inventive method, ultrasonic signals from various aspect angles along the scan are combined to improve the reliability of defect detection. The multi-angle system reinforcement technique will also improve defect signal strength above background noise. This results in fewer false defect indications.

The received pulses from each location of the scan is detected and stored, in complex form, in digital memory. For each location on the material which was scanned, not only the signal of the transducer or transducer array for that location is used but also the signal from other locations in the scan. The signals from the other locations are multiplied by the corrective phase shift factor to compensate for the time delay of the ultrasonic pulse from these other locations. The amount of phase shift correction of course increases with the angle of incidence. The signals from the scan positions are each thus rotated so that they add or reinforce each other. A signal average for each location along the scan is thus computed by using the appropriate phase shift rotation for each recorded signal. Laboratory experiments have indicated that the probability of detection and signal-to-noise ratio can be improved by using this technique. The signal reinforcement technique improves flaw detectability by increasing the signal to noise ratio. The ultrasonic beam information which was sampled during the dynamic mode of scanning is later combined to provide a composite signal of the material characteristics at each location along the scan. The material characteristic is a function of many different aspect angles.

The inventive composite signal approach will reinforce or enhance volumetric deflections (such as flaws) due to their interaction with the ultrasonic beam from multiple angles. According to the inventive technique, signals which are generated due to the characteristic internal material structure (such as grain) will be deemphasized due to their directionality and relative acoustic impedance which do not yield multiple reflections from different aspect angles that constructively combine vectorially to comparable magnitudes. Multiple reflections from different aspect angles do occur when an actual flaw is present. This results in an improved volumetric inspection technique for material characteristics and flaw detection.

Although the invention primarily makes use of digital processing techniques, the phase sensitive construction of a composite material response can be implemented with multielement or single element transducers that combine signals in analog form.

Accordingly an object of the present invention is to provide a method for the ultrasonic testing of a material, comprising transmitting ultrasonic waves into the material for producing reflected signals which are characteristic of internal structures of the material, detecting the reflected signals at a plurality of locations which are distributed along a scan path over the material, storing the detected reflected signal for each location and producing a composite signal for each individual location. The composite for each individual location is obtained by multiplying the detected reflected signal of each other location by a corrective phase shift factor which is a characteristic of the individual location and which compensates for a time delay of the detected reflected signal from the other locations to the individual location, to obtain a rotated reflected signal for each other location and adding together the signal from the individual location with the rotated reflected signals from each other location to produce the composite signal.

A further object of the invention is to provide an apparatus for achieving the inventive method.

The various features of novelty which characterize the invention are pointed out with particularity in the claims annexed to and forming a part of this disclosure. For a better understanding of the invention, its operating advantages and specific objects attained by it uses, reference is made to the accompanying drawings and descriptive matter in which a preferred embodiment of the invention is illustrated.

BRIEF DESCRIPTION OF THE DRAWINGS

In the drawings:

FIG. 3 is a flow chart showing a program which can be utilized to practice the invention.

DESCRIPTION OF THE PREFERRED EMBODIMENT

Figure 1:
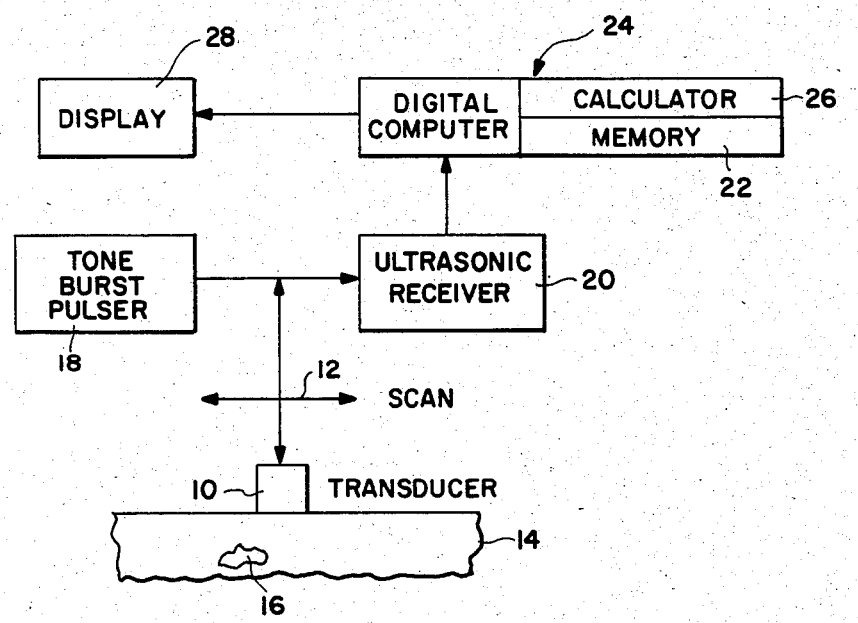
FIG. 1 is a block diagram schematically showing apparatus which can be used to practice the invention.

As shown in FIG. 1, the invention utilizes a transducer or array of transducers 10 which can be moved or sequentially activated in a scan direction 12, over the surface of a material 14 to be tested. The object of the invention is to use ultrasonic waves which are transmitted into the material 14 to detect the presence of flaws or defects 16. This is despite the coarse grained structure which may make up the material 14. Such materials include cast metal, stainless steel, and inconel.

Ultrasonic waves which are transmitted into the material 14 are generated by a tone burst pulser 18 which can use the same or a different transducer. An ultrasonic receiver 20 is connected to the transducer or transducer array 10. The reflected ultrasonic signals from material 14 are converted into digital form and stored in the memory 22 of a computer generally designated 24. Computer 24 also includes a calculator 26 whose purpose will be described later. A display 28 is connected to computer 24 for displaying the results in a graphic or numeric manner.

Figure 2:
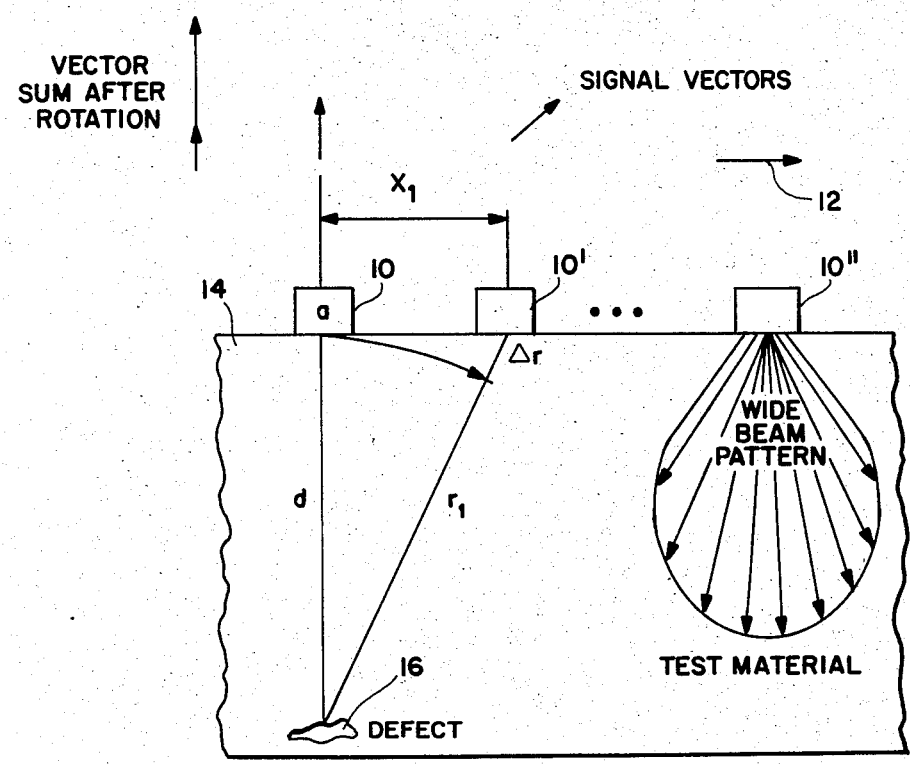
FIG. 2 is an explanatory diagram showing a piece of material to be tested and three test locations lying on a scanned path over the material.

As shown in FIG. 2, a set of signals is generated by sampling reflected ultrasonic signals at a plurality of spaced locations in the scan path 12. These are designated at 10, 10' and 10''. The distance between each scan location is shown at $X_i$. An individual location of transducer 10 which is designated a, is at a distance d from a defect 16. The distance from the transducer 10' is the distance $r_i + \Delta r$. This distance represents a time delay for the propagation of a reflected signal from defect 16 to transducer or transducer position 10', with respect to the position a.

According to the invention, the reflected signal at location a is taken as not only the reflected ultrasonic signal to the transducer at that location, but also the summation of contributing signals from each of the other locations both before (not shown) and after location a. The contribution of each other location is multiplied by a corrective phase shift factor that coresponds to the delay time and can be thought of as a vector rotation factor R.

By storing the signal from each transducer location along the scan path in memory 22, the reflected signal of all the locations can be used to analyze each individual location.

As shown in FIG. 2, the ultrasonic wave transmitted from transducer 10'' is in the form of a wide band pattern containing vectors extending in various directions. This vector characteristic of the travelling wave may be used to enhance the signal received from any individual one of the locations on the material. According to the invention the back scattering energy, due to the granular nature of the material, is compensated for or substracted out by adding together the effects, suitably weighted, from all of the other locations at the individual location of interest. Each individual location is analyzed in turn to determine the presence of defects such as the defect 16. This enhances the signal-to-noise ratio.

The signal from each other location is multiplied by the rotation factor which can be calculated as follows:

Vector Rotation Factor (R):

$$R = e^{j2Kr_i}$$

$$K = 2\pi/\lambda$$

$$r_i = (d^2 + x_i^2)^{\frac{1}{2}}$$

$\lambda$ = wavelength

Total Signal ($S_T$) Computed for Position "a":

$$ST_a = \sum_{i=-N}^{N'} (S_{a+i})(e^{j2K(d^2 + X_i^2)^{\frac{1}{2}}})$$

N = number of signal data samples before position "a"
N' = number of signal data samples after position "a"
$S_{a+i}$ = unrotated signal received at position (a+i)
$x_i$ = scan distance from position "a" to position a+i.
  $x_{a+i} = i\Delta x$ when data are taken at equal multiple increments along x.
i = data number
a = lateral position for computation of signal sum
d = depth beneath surface Displayed Signal:

$$SD_a = S_T = (SR_a^2 + SI_a^2)^{\frac{1}{2}}$$

signal amplitude at position a.

$SR_a$ = Real part of complex sum, $S_T$, at position a.

$SI_a$ = Imaginary part of complex sum, $S_T$, at position a.

As shown above, the total signal $S_T$ which is computed for each individual location a, is a function of the summation of the signal from that location plus the signal, suitably weighted by the rotation factor, from each of the other locations. There are assumed to be N+N' locations in all in the scan path 12. The displayed signal $S_D$ is equal to the absolute value of the composite signal $S_T$ which is a function of both the real and the imaginary part of the complex signal. According to the invention both the complex and the real part of each signal is stored in memory 22.

FIG. 3 is a flow chart showing the calculations which can be performed by the calculator 26 of computer 24. In box 31 the initial known values are supplied to the calculating section, such as the wave length, the distance between sampling locations, the depth of the material to be interrogated (z) and the scanning angle (α). The ultrasonic system shown at 31 inputs the reflected signals for storage in memory. In box 32, two phase sensitive scan blocks of data are generated which are separated by 90° to each other. The ultrasonic inspection was implemented by electrically mixing a reference sinusoidal signal with the time gated tone burst reflected from the material. To determine both phase and quadrature, two linear scans across the material were taken. On the second scan the reference signal was shifted 90° from the initial reference signal. In both cases, reference or reference plus 90°, the ultrasonic signal was mixed in a double balanced mixer to provide the in-phase (or real) and the quadrature (or imaginary) components of the received voltage.

The dual sequence of scanning to obtain phase and quadrature was used on various test blocks to verify the results of the invention. Typically a four or six inch scan was made to collect 1024 data points or locations, at equal intervals in the scan path. The algorithm combined the two scans to compute a composite point-by-point sum which was displayed graphically. A H-P Fast Fourier analyzer and analog electronic instrumentation was utilized to process the signals.

Block 33 of the computer produced the rotational factor for each location. In block 34 the real and complex components of the signal from each location was stored. The multiplication step took place in box 35 wherein the rotation factor is applied to each vector. The summation for each individual point takes place in box 36 and magnitude for the display 28 is calculated in box 37. This outputs a signal to box 38 which can be connected to display 28. Actual experiments conducted with metal specimens through which holes were drilled to simulate defects confirm a correlation between the composite signal from each location and the presence of the defect (drilled through hole).

While a specific embodiment of the invention has been shown and described in detail to illustrate the application of the principles of the invention, it will be understood that the invention may be embodied otherwise without departing from such principles.

What is claimed is:

1. A method for the ultrasonic testing of a course-grained material, comprising:
   transmitting ultrasonic waves into the material to produce reflected signals which are characteristic of internal structures of the material;
   detecting the reflected signals at a plurality of spaced locations distributed along a known scan path over the material;
   storing the detected reflected signal for each location;
   for each individual location, multiplying the stored detected reflected signal for each other location by a corrective phase shift factor which is characteristic of a time delay for the detected reflected signal from the other locations to the individual location, to obtain a rotated reflected signal for each other location; and
   for each individual location, adding the rotated reflected signal for each other location to the reflected signal for the individual location to form a composite signal, designated $ST_a$, indicative of internal structures in the material, which equals:

$$\sum_{i=-N}^{N} (S_{a+i})(e^{j2K(d^2 + X_i^2)^{\frac{1}{2}}})$$

wherein N is the number of locations before an individual location a, N' is the number of locations after position a, $S_{a+i}$ is the reflected signal at each position a+i, i being a number designating each individual location, $X_i$ is the distance between each adjacent location along the scan path, and d being the depth from a surface of the material to the internal structure which causes the reflected signal.

2. An apparatus for the ultrasonic testing of a coarse-grained material, comprising:
   a tone burst pulser for generating an ultrasonic wave for transmission into the material;
   transducer means, connected to said tone burst pulser, for applying the ultrasonic wave to the material and for receiving a reflected ultrasonic signal back from internal structures of the material;
   scanning means connected to said transducer means for receiving a reflected ultrasonic signal from a plurality of spaced locations lying on a known scan path extending across the material;
   a memory connected to said transducer means for storing a reflected signal from each location on the scan path; and
   calculator means connected to said memory, for calculating a composite signal, designated $ST_a$, for each location, indicative of internal structures in the material, which is equal to the summation of a reflected ultrasonic signal at each individual location plus a rotated reflected signal from each other location spaced from the individual location which rotated reflected signal is equal to the reflected signal at each other location multiplied by a phase shift factor which corresponds to a time delay for a reflected signal from each other location to the individual location, according to the relationship:

$$ST_a = \sum_{i=-N}^{N} (S_{a+i})(e^{j2K(d^2 + X_i^2)^{\frac{1}{2}}})$$

wherein N is the number of locations before an individual location a; N' is the number of locations after position a; $S_{a+i}$ is the reflected signal at each position a+i, i being a number designating each individual location; $X_i$ is the distance between each adjacent location along the scan path; and d being the depth from a surface of the material to the internal structure which causes the reflected signal.

* * * * *

UNITED STATES PATENT AND TRADEMARK OFFICE
CERTIFICATE OF CORRECTION

PATENT NO.  :  4,640,132
DATED       :  Feb. 3, 1987
INVENTOR(S) :  Flora et al.

It is certified that error appears in the above-identified patent and that said Letters Patent is hereby corrected as shown below:

In Col. 4, line 15, "a" should read --$\underline{a}$--.

In Col. 4, line 20, delete "coresponds" and insert therefor --corresponds--.

In Col. 4, line 43, delete "R = $e_{j2Kr}i$" and insert therefor --R = $e^{j2kr}$--.

In Col. 6, line 17, in the first formula, immediately after the first "N", insert --'--.

In Col. 6, line 56, in the second formula, immediately after the first "N", insert --'--.

Signed and Sealed this

Nineteenth Day of June, 1990

Attest:

HARRY F. MANBECK, JR.

*Attesting Officer*  *Commissioner of Patents and Trademarks*